(12) United States Patent
Warren et al.

(10) Patent No.: US 7,770,729 B2
(45) Date of Patent: Aug. 10, 2010

(54) ARRAY OF MULTI-STAGED CLEANING WIPES

(75) Inventors: Adam Matthew Warren, West Chester, OH (US); Markus Rosar, Birkenfeld (DE); Marita Alegre de Miquel, Liederbach am Taunus (DE); Natascha Kreuzer, Hofheim am Taunus (DE); Jane Hooper Welling, Cincinnati, OH (US); Joyce Marie Benjamin, Mason, OH (US); Joshua James Norman, Cincinnati, OH (US); Melissa Marie King, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 332 days.

(21) Appl. No.: 11/415,709

(22) Filed: May 1, 2006

(65) Prior Publication Data
US 2007/0251851 A1 Nov. 1, 2007

(51) Int. Cl.
*B65D 85/00* (2006.01)
(52) U.S. Cl. .................. 206/440; 206/459.5; 206/494
(58) Field of Classification Search .............. 206/581, 206/440, 459.5, 494, 233, 449, 572, 570; 221/50, 1, 2; 40/312
See application file for complete search history.

(56) References Cited

U.S. PATENT DOCUMENTS

| | | | |
|---|---|---|---|
| 4,117,187 A * | 9/1978 | Adams et al. ............... | 442/118 |
| 5,231,266 A | 7/1993 | Warren | |
| 5,368,188 A * | 11/1994 | Twardowski ................. | 221/50 |
| 5,947,302 A | 9/1999 | Miller | |
| 6,190,369 B1 * | 2/2001 | Palumbo et al. ........ | 604/385.01 |
| 6,361,784 B1 * | 3/2002 | Brennan et al. ............. | 424/402 |
| 6,500,444 B1 * | 12/2002 | Ferenc et al. ............... | 424/404 |
| 6,581,775 B1 | 6/2003 | Hagopian | |

(Continued)

FOREIGN PATENT DOCUMENTS

EP 1 695 742 8/2006

(Continued)

OTHER PUBLICATIONS

U.S. Appl. No. 11/066,091, filed Feb. 25, 2005, Norman.

(Continued)

*Primary Examiner*—Ehud Gartenberg
*Assistant Examiner*—Andrew Perreault
(74) *Attorney, Agent, or Firm*—Amy M. Foust; Matthew P. Fitzpatrick

(57) ABSTRACT

An array of multi-stage configured cleansing wipe products may include first stage cleansing wipes and second stage cleansing wipes. The first stage cleansing wipes may have a first structure and a first composition selected in view of a first child developmental stage. The second stage cleansing wipes may have a second structure and a second composition selected in view of a second child developmental stage. The first structure and the first composition are different and potentially progressive from first stage to second stage. First stage product packaging may include at least one first stage-specific indicia and second stage product packaging may include at least one second stage-specific indicia. Stages of the array may be communicated and tailored based upon the foods eaten and the manner of eating (such as being fed or self-feeding) of the babies or children in each stage.

19 Claims, 2 Drawing Sheets

U.S. PATENT DOCUMENTS

| | | |
|---|---|---|
| 6,648,864 B2 | 11/2003 | Ronn et al. |
| 6,667,464 B2 * | 12/2003 | Ellis .......................... 219/400 |
| 6,763,944 B2 | 7/2004 | Ronn et al. |
| 6,830,755 B2 | 12/2004 | Librizzi et al. |
| 6,837,395 B2 | 1/2005 | Windorski et al. |
| 7,572,249 B2 | 8/2009 | Betts |
| 2001/0055609 A1 | 12/2001 | Shantz et al. |
| 2002/0072723 A1 | 6/2002 | Ronn et al. |
| 2002/0164910 A1 | 11/2002 | Murray |
| 2003/0019508 A1 * | 1/2003 | Tomarchio et al. ............. 134/6 |
| 2003/0120231 A1 * | 6/2003 | Wang et al. ................. 604/368 |
| 2004/0030308 A1 | 2/2004 | Ronn et al. |
| 2004/0052834 A1 | 3/2004 | West et al. |
| 2005/0074483 A1 | 4/2005 | Lange |
| 2005/0121347 A1 | 6/2005 | Hanson |
| 2005/0133387 A1 | 6/2005 | Cohen et al. |
| 2005/0142336 A1 | 6/2005 | Romano, III et al. |
| 2006/0173695 A1 * | 8/2006 | Brandt .......................... 705/1 |
| 2006/0186132 A1 * | 8/2006 | Panning et al. ................. 221/2 |
| 2006/0193898 A1 * | 8/2006 | Norman ..................... 424/443 |
| 2006/0195357 A1 * | 8/2006 | Klofta et al. ................. 705/14 |

FOREIGN PATENT DOCUMENTS

| | | |
|---|---|---|
| GB | 1 603 780 | 11/1981 |
| WO | WO 2005/039511 A | 5/2005 |

OTHER PUBLICATIONS

PCT Search Report, mailed Jan. 31, 2008, 3 pages.
http:www.wilkinsonplus.com/content/ebiz/wilkinsonplus/invt/0253659/0253659 1.jpg.

* cited by examiner

ARRAY OF MULTI-STAGED CLEANING WIPES

FIELD OF THE INVENTION

This invention relates to the design, specification and configuration of products and product packaging for an array of multi-stage configured consumer products such as personal cleaning wipes.

BACKGROUND OF THE INVENTION

Many products are developed and marketed as multi-purpose and convenient in that one product replaces many products. Cleaning products provide an example where a single product is represented as replacing several specially designed products—one cleaning product replaces specially designed glass, surface and floor cleaners. Such a product is often a compromise in certain features or attributes, and the one-size-fits-all approach can and often does result in a product that is perhaps competent for all of the intended applications, but that does not excel in each application.

Other products are specially developed for single, specific applications. For these products, the consumer purchases the specialized product for the associated application. Even when a consumer is aware of the best combination of characteristics desired in a given product, there may be difficulty in finding the correct product for the intended application. This is particularly true where the product may be a member of a group of related products, wherein each member product of the group is designed with specific characteristics.

Guiding the consumer to the correct product may be especially difficult where the products otherwise appear to have similar characteristics, but in fact, they have different characteristics that allow them to perform better for one application over another application. Furthermore, because the products may be positioned together, as in a line-up or array of products, within a retail display. They may have similar appearance, packaging and trademarks and the like.

Because consumers can be hurried in the purchase decision, the consumer may end up with the wrong product and may have to return the product and purchase the correct product. Alternately, the consumer may use the incorrect product, and not realize the full benefit that would have otherwise been achievable with the correct product. Worse, the consumer may use the incorrect product and perceive the product to be poorly designed or made because it does not perform well, where in fact it is the wrong product for that consumer's application. Product suppliers work hard to maintain consumer satisfaction and loyalty, which can be compromised by one bad experience.

Products to be used by or for babies or small children such as diapers, wet wipes, bottles, formula, training pants and the like are typically referred to generically as "baby care" products. Such products are often grouped and sold together in a common location of a retail established such as the "baby" aisle of a grocery store. It is common for consumers shopping for such products to have young children or babies with them while shopping and such consumers often have very limited time and attention to devote to locating and selecting a particular product offering. Therefore, there is need to communicate clearly, quickly, and effectively the proper product characteristics to consumers and to maximize the likelihood that the most appropriate product or products is selected for a given use situation. As noted, this can be particularly important for products specialized to specific tasks within a line-up array or of product offerings.

Some brands of baby wipes products are currently sold in multiple versions creating an array of wipes products organized under that brand. Typically, these current arrays offer such variations as scented and unscented wipes, wipes including skin-care ingredients such as aloe and those without such additional ingredients, or wipes in differing packaging forms such as hard tubs and flexible film packaging. Additionally, some baby care products such as disposable diapers, are currently sold in a "stages of development" format. An example such a format is PAMPERS SWADDERS, PAMPERS CRUISERS, PAMPERS EASY UPS, and PAMPERS FEEL N' LEARN line up which has a common icon scheme with product features varying as appropriate for the baby's stage of development.

In the context of disposable diapers, the concept of product stage is primarily related to the size, movement, and fit characteristics needed by the products. Many consumers appreciate that young babies grow rapidly and have different movement characteristics, as well as physical size differences, as they grow. Therefore, consumers may appreciate and expect that diaper product design changes as appropriate to meet these changing fit, movement, leakage prevention, size, and other needs. An example of effective mechanisms to offer and communicate these and related stage appropriate performance characteristics (such as training features) is described in U.S. Pat. Nos. 6,763,944 and 6,648,864.

While other baby care products such as disposable wet wipes have been sold in various product versions, these have not typically been customized on the basis of stage of child development and products have not necessarily been tailored to meet the needs which are characteristic of a given stage of development. In contrast to such product offerings, the arrays of multi-stage cleaning wipes described herein are tailored to correspond to the cleaning needs characteristic of each stage of development.

DETAILED DESCRIPTION OF THE INVENTION

Figure 1:
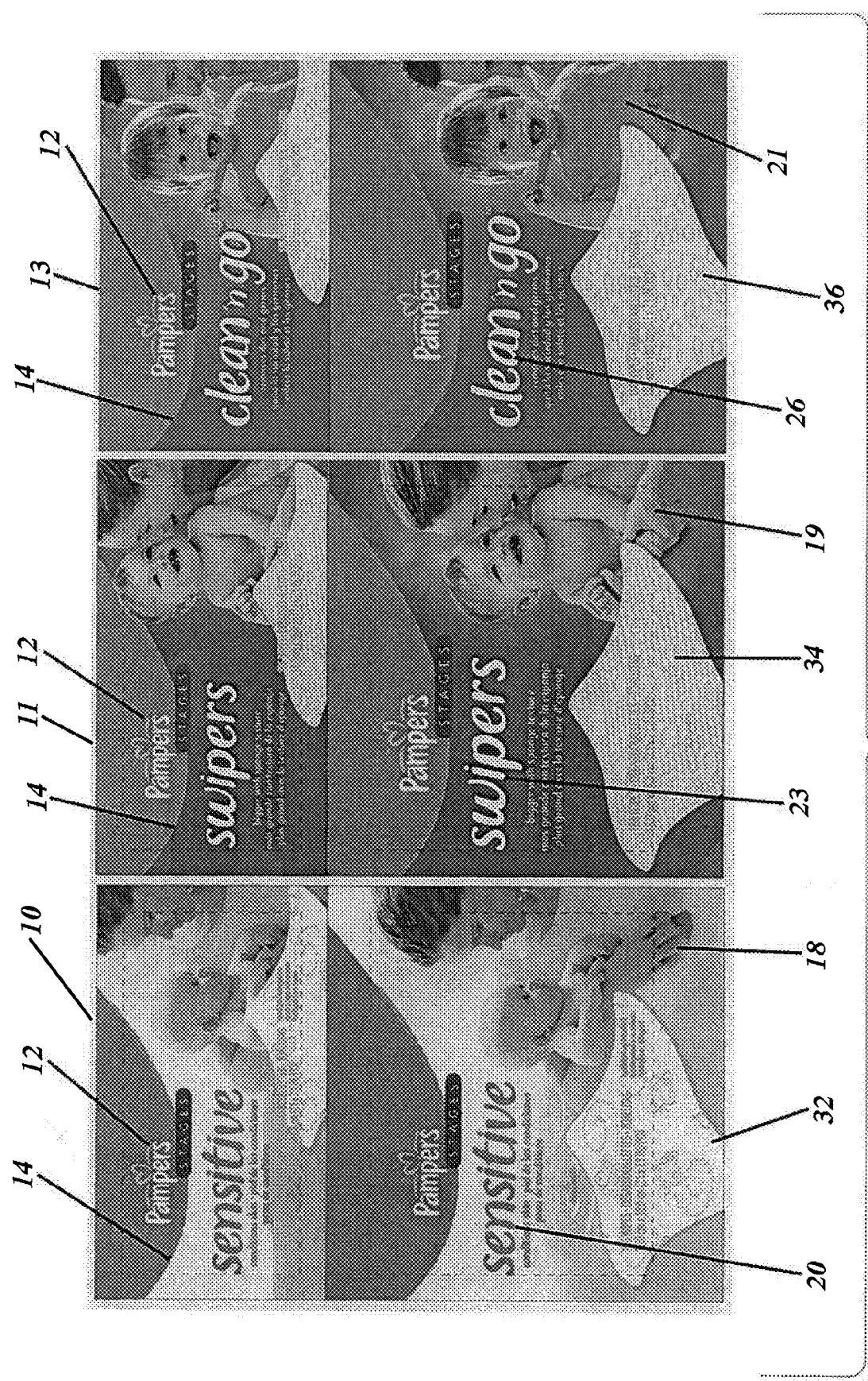
FIG. 1 illustrates an array of three wipes product offering and packaging in accordance with one of the herein described embodiments.

The following terms will have the indicated definitions for purposes of the present specification, including the claims.

As used herein, the term "lotion load" refers to the weight of cleaning lotion applied to a substrate as a percentage of the weight of the substrate. For example, a 2 g substrate with a 340% lotion load would have 6.8 g of cleaning lotion impregnated into it.

"Formula" or "baby formula" refers to a milk, mixture, or substitute for feeding an infant. Formula is generally designed to simulate breast milk and breast milk itself is intended to be included within the definition of formula as used herein. Formula is typically a low viscosity liquid as prepared and is available commercially in several brands and varieties.

"Cereal" refers to food made of grain, typically prepared for infants as a high-viscosity liquid. Cereal may be fed to an infant via a spoon or a bottle. Cereal in the form discrete solid particles (such as "flakes") is typically eaten by older children and adults and is a form of table food. For purposes of the instant definition a cereal which is not a high viscosity liquid is not considered to be a cereal.

"Jar foods" are foods specifically prepared to be fed to infants as a high viscosity liquid. Specific examples include strained peas, carrots, apples, applesauce, bananas, etc.

"Table food" refers to food typically eaten by adults. For children and babies table foods may be cut into small pieces and/or served in smaller portions.

A group of products may be configured wherein each product within a group of related products is specially prepared, i.e., designed, specified and tested, for particular related applications. Baby Care type products in particular may be tailored to correspond to particular stages, for example, to reflect the manner in which parents tend to think of children growing through various "stages of development." The product stages may further facilitate the purchase decision and direct the consumer to the correct product for the consumer's needs. The products within the group may have a number of common characteristics and yet still have particular characteristics tailored to specific needs. For example, the products may have a common use, such as cleansing wipes, may have common structural characteristics and composition, such as substrate, lotion, perfume and packaging elements.

For an exemplary cleansing wipes product, the structure and composition of the products for each stage may be specified to meet specific needs of infants during various phases of development from new-born through toilet training. Such structural elements of the cleansing wipes within the array of cleansing wipes may differ in the specific structural elements of substrate type, substrate texture, lotion type, lotion load, differences in surfactantcy of the lotion, the presence or absence of skin-conditioning agents in the lotion, the presence or absence of anti-stick agents in the lotion, and/or the presence or absence or level of scent in the lotion.

For example, babies from birth to about 6 months of age (referred to in this example as Stage 1) typically nurse or are fed formula or breast milk exclusively or nearly exclusively. Additionally, newborn skin tends to be more sensitive, in general, than that of older babies and children. Babies in this stage tend to have runny bowel movements (BMs) due to the level of development of their digestive systems and the dominance of formula and/or breast milk in their diets.

It may be desirable for a cleaning wipe tailored for this stage to be capable of readily absorbing such runny BMs and urine. Uptake of liquid (e.g. runny BMs) may be affected by control of pore size, pore distribution and void volume of the substrate to achieve good lotion acquisition and capillary action in the wipe. The texture of the wipe may be lower than that of later stages as mess is primarily being absorbed rather than "wiped", "scrubbed", "lifted" or "scooped." A suitable substrate may be 60% polypropylene and 40% viscose blend of about 58 gsm.

A cleaning wipe tailored for Stage 1 may comprise a cleaning lotion which comprises about 0.1% AbilCare® and about 1% glycerine and a pH buffer. The suitable lotion may have low-level surfactantcy. Surfactantcy as used herein is a measure of the cleaning ability of the product. High surfactantcy is typically indicated by high levels of surfactants and/or surfactants with high HLBs (hydrophile lipophile balance). Alternately, low surfactancy is indicated by low levels of surfactants and/or surfactants with low HLBs. The low-level surfactancy provided by the 0.1% AbilCare® may provide a mild, gentle, cleaning benefit without irritating the newborn's skin. The presence of the glycerin may be appropriate for the stage 1 wipe lotion as it may provide conditioning for the newborn's more gentle skin. Other skin conditioning agents as a substitute for or in addition to glycerin may also be included.

A cleaning wipe tailored for Stage 1 may have a lotion load of 340% (w/w % taken as weight of lotion per weight of substrate) or less. In order to facilitate the uptake of the runny BM, it is not desirable for the lotion load of the Stage 1 wipe to be too wet, yet it is also desirable that the lotion load be sufficiently high to provide for gentle cleaning, including providing a lubricity for the wipe relative to the skin during cleansing.

A cleaning wipe tailored for Stage 1 may have no perfume or odor control feature or may include a perfume or scent at low levels, if desired. One of skill in the art will recognize that it may be desirable to include a scent or perfume in a wipe product to offset any impact the natural scent of the cleaning composition may have. However, high levels of such scent or perfume may not be needed such as such levels may be irritating to the newborn's skin and/or may be perceived by the care-giver as being irritating to the newborn's skin. As used herein scent or scent level refers to the total perceived fragrance impact of the product as provided in its commercial form and can be determined by a panel of expert odor graders on a 10 point scale.

A cleaning wipe tailored for Stage 1 may have a package that may be a white frosted tub to convey the gentleness of the product. Other packaging elements or descriptors may be chosen to convey attributes such as nourishing, conditioning, soft and gentle, milk essentials, hypoallergenic, perfume free, or combinations of these. It will be appreciated that the ages given above for this and the remaining stages are approximate and may vary for different babies and children.

Babies from about 6-18 months old (referred to in this example as Stage 2) typically eat solid or semi-solid food including cereal and jar-foods, either exclusively or with some nursing or formula feeding. With or without continued nursing or formula feeding, the additional foods in the diet combined with a maturing digestive system leads to different BM characteristics as compared to Stage 1. BMs in this stage of development tend to be "sticky", and will adhere more to skin. BM's in this stage of development also tend to have stronger or more offensive odors associated with them than BM's associated with Stage 1.

The cleaning wipe tailored for Stage 2 may be thicker and bigger that that tailored for Stage 1. The substrate may also be more highly textured than a substrate tailored for Stage 1, as removal of the sticky BM's may require "scrubbing". A texture appropriate for a Stage 2 cleaning wipe may have a texture such as with a "soft sponge like" texture for better cleaning of sticky BMs. A suitable substrate may comprise about 60% polypropylene and about 40% viscose blend and have a basis weight exceeding about 58 gsm.

The cleaning lotion may comprise about 0.45% AbilCare® and in general may have higher surfactancy than the lotion(s) tailored for Stage 1. The higher surfactancy may facilitate the removal of the sticky BM's, and may not pose that same level of concern to the gentle skin of the newborn, as the baby's skin has matured.

The lotion load may be similar to or higher than that of the Stage 1 and may be about 340% (w/w % taken as weight of lotion per weight of substrate). Hydrating the BM for cleanup may be more necessary at this stage than for Stage 1 (where absorption may be primarily desired) and this hydration may be facilitated by the higher relative lotion load. Additionally, an anti-stick agent to aid in removal of sticky BMs may also be included in cleaning lotions tailored to this stage.

Scents and/or odor control technologies may be included and relatively high levels of odor masking scents and/or odor control technologies may be desired. The Stage 2 BM's may have stronger and more offensive odors and the higher scent levels and/or inclusion of odor-masking and/or odor-absorption technologies may be desirable. The higher scent levels and/or higher levels of odor-masking and/or odor-absorption technologies may not pose that same level of concern to the gentle skin of the newborn, as the baby's skin has matured.

The package may have a "jelly" frosted tub to indicate an older stage and "sticky" nature of the mess to be cleaned. Other packaging elements or descriptors may be chosen to convey attributes such as cleans difficult messes, thick and generous size wipe, picks up more with each wipe and combinations of these.

Babies from about 18 months and older (or until about the age of toilet training, referred to in this example as Stage 3) typically, eat a varied diet of table-foods consisting of solid food and drinks similar to adult foods cut into smaller pieces and in smaller portions. BMs in this stage tend to be even more solid than BM's in Stage 2. Additionally, children in this stage may be feeding themselves at least some of the time, either with their hands or with utensils, and in any event may get food on their hands and face at mealtimes. Cleaning wipes in Stage 3 are often used on the hands and face in addition to diaper changes at this stage. Cleaning wipes in Stage 3 are often used by the child in cleaning their own face and hands.

Stage 3 BM is more solid than in stage 2 and may need to be "scooped" or "lifted" with the wipe. The wipe may need to act as a barrier and it may be desired to have more opacity to eliminate the ability to see the mess through the wipe. The substrate at this stage may be particularly strong to reduce tearing, particularly when the child may be cleaning his/her own face and hands, and may be stronger than the substrate in either Stage 1 or Stage 2. The substrate may be more textured than stage 1, but less textured than stage 2. A suitable substrate may also be about 60% polypropylene and about 40% viscose with a "dew drop" texture.

The lotion may comprise about 0.1% AbilCare®. The lotion may have a moderate or low surfactancy. The surfactantcy of the lotion may be less than that of the Stage 2 lotion and equal to or higher than that of the Stage 1 lotion. The relatively higher level of surfactantcy of the Stage 2 wipe lotion may not be required in the Stage 3 lotion as the BM's do not adhere to the skin to the same degree, and the lower level of surfactancy in the Stage 3 wipe lotion may be desirable as the wipe is used on the face and hands, where high surfactancy may be undesirable. The lotion may contain anti-bacterial agents that help mitigate microbial growth on the skin.

The lotion may be loaded at about 315% (w/w % taken as weight of lotion per weight of substrate). The relatively higher lotion load of the Stage 2 wipe lotion may not be required in the Stage 3 lotion as the BM's do not require as much hydration for effective removal, and the lower lotion load in the Stage 3 wipe may be desirable as the wipe is used on the face and hands, where residual lotion on the skin may be particularly undesirable.

Moderate levels of scent may be desired and the perfume amount may be less than that for Stage 2 but more than that for Stage 1. The need to mask the malodor of the BM's is not as great as that of the Stage 2 lotion, and the anticipated use of the wipe in cleaning face and hands may make the use of high levels of scent, undesirable.

The package may be flexible film packaging with a fitment for use in a variety of situations including outdoors and at restaurants and the like. Other packaging elements or descriptors may be chosen to convey attributes such as removes dirt and germs from the hands and face and bottom, tear free and combinations of these.

The amount of texturing as used in the descriptions above refers to the total amount and size of deviations from a planar surface a substrate is provided with. Thus a non-textured surface is essentially flat in an x-y plane. A low total area of texturing elements (such as embossing, or molding elements) as a function of overall substrate area and/or small height differential from the flat substrate plane of such elements represents low texturing. By contrast a highly textured surface has texturing characterized by high total textured surface area and/or large height of such texturing elements (compared to the "flat" plane of the substrate).

An optional fourth stage (not shown) may be a toilet training stage. A wipe product such as a flushable toddler wipe may be offered for this stage. The substrate may be sized to be toilet paper sized (to reinforce the use with the child) and may be made to be flushable. Lotion and perfume content are no longer required in significant quantity, but scents that appeal to a child may now be used to again encourage the child into good habits. At this point also the packaging may be made to include stage specific indicia that appeals to the child.

It can be appreciated from the foregoing, that the product characteristics are specified to provide a desired performance consistent with a child's development. In particular, characteristics of the product are selected in view of what and how the child is feed. The product may be specified in view of other developmental qualities of the child.

In order to further ensure that the consumers are able to regularly and reproducibly identify and purchase the product which is most appropriate to their child's developmental needs, it is further important to ensure that the product package quickly and effectively communicate the attributes and intended use of the products contained therein, while maintaining the common packaging elements of the product line-up.

The common packaging elements, identifying the products as cleansing wipes of a particular brand, and may further include indicia to quickly draw the consumer to the correct product to meet their child's current cleansing wipe need. The products may be may be virtually any product but typically the products may be grouped based upon a common use or characteristic, e.g., cleansing wipe; feminine hygiene product, diaper, cleanser, etc, and may typically permit specification in stages. The stages may be progressive, and for the cleansing wipe example, these may be age or developmentally based associated with an infant/child, but the stages need not be progressive, may be regressive or may not be temporally related.

In the embodiment illustrated in FIG. 1, the products are an array of cleansing wipes that may be used for infants and young children. Each of the first package 10, second package 11, and third package 13 includes a number of indicia including a brand name 12, a common indicia 14, e.g. a color wave. The package 10 may further include a stage-specific indicia 18, e.g., an adult and stage appropriate picture of a baby or child, and another stage-specific indicia 20, e.g., a stage-related word or description. The stage appropriate picture of a baby or child may further include a picture of a stage appropriate baby or child being fed by a stage appropriate means.

FIG. 1 further illustrates how stage indications may vary across the products of the array. For example, first package 10 corresponding to a first stage may have a first stage photographic indicia 18. FIG. 1 shows a mother holding an infant in her arms. This provides a quick visual indication that the wipe product is designed for children in a first stage of development of approximately 0-6 months of age. The inclusion of an adult helps provide a frame of reference to more readily identify the stage of child depicted in the photograph or icon with the adult. Second package 11 corresponding to a second stage of development of approximately 6-18 months of age may depict a second stage icon or photograph 19. In this case a mother holding sitting up older baby is shown. A third package 13 corresponding to a third stage of development of approximately 18 months and older may contain a third stage icon or photograph 21. In this case the photograph shows a father with a young boy of approximately 18 months of age or older feeding himself and getting some food on his face. All three packages shown in FIG. 1 include the brand name indicia 12, and common design indicia 14 that assist in identifying the product contained by the package as being part of the product group from a particular manufacturer or supplier. Each of the first package 10, the second package 11, and third package 13 may further includes stage-specific indicia, e.g., a mother with an exploring, i.e., crawling young baby and stage-specific indicia 20, 23, 26 such as a stage-related word or description. Additionally, each package may include a representation of one or more product features such as substrate representations 32, 34, and 36 which show how features of the products may vary across the array. Additionally each product may include a scent-descriptor such as "unscented".

The common indicia 14 and 12 convey a message to the potential consumer that the products are from a particular manufacturer or source and have a common general use. The stage-related indicia 18, 19, 21, 20, 23, and 26 convey a message to the potential consumer of a specific category of use under the general use for which the product is specialized.

There are numerous possible indicia that may convey the stage-specific message. For cleansing wipes, as an example, the stage may be conveyed by any of: representations of the child age, depiction of a mother and child, depiction of a father and child, a child eating by nursing, eating spoon foods, starting solid foods, self feeding, etc. and/or activity of the child by depicting crawling, walking, etc. Icons showing types of foods eaten, or manner of eating may be used to represent the stages in a cleaning wipe array.

Figure 2:
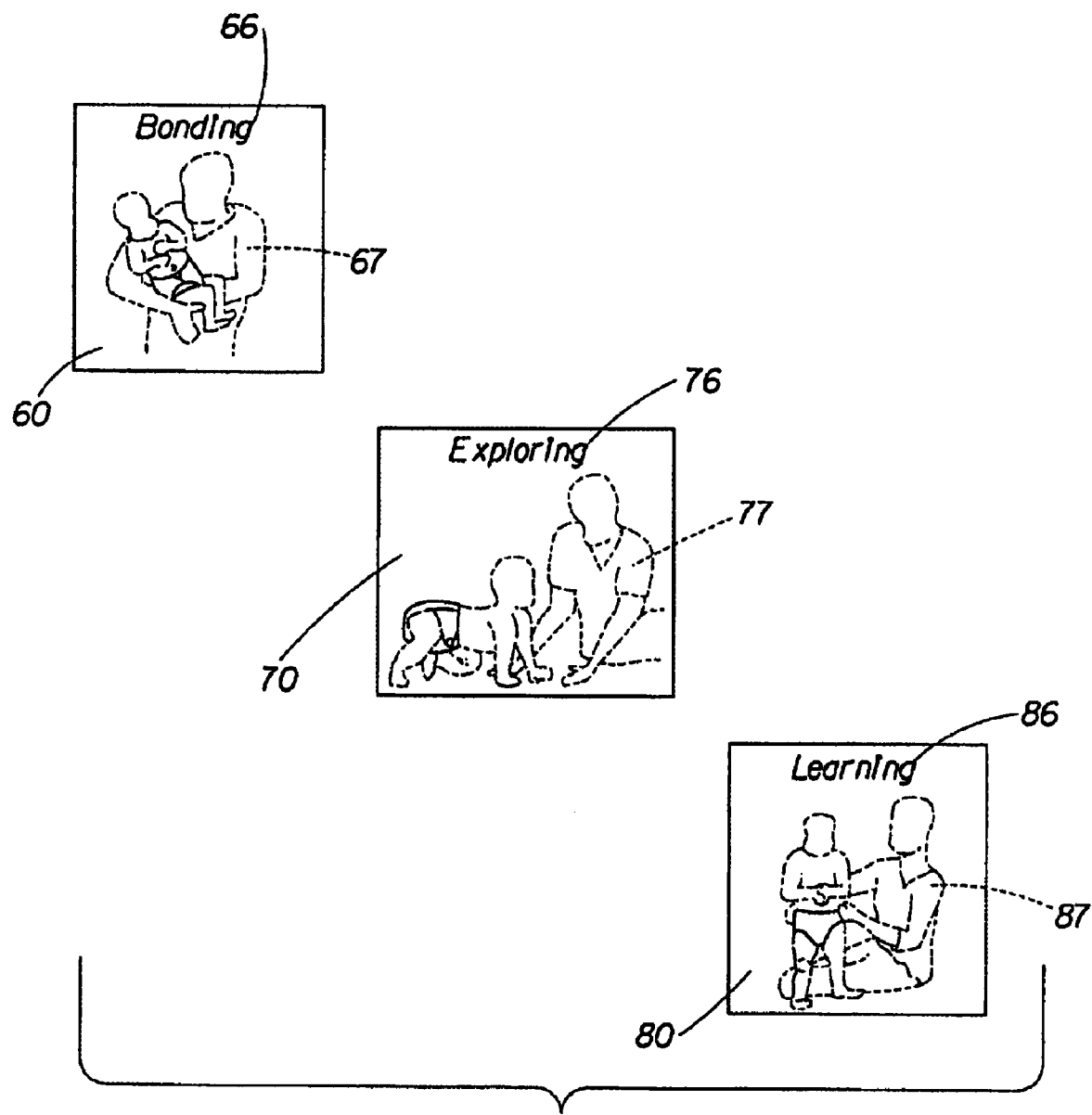
FIG. 2 illustrates products of a product group having multi-stage configuration in accordance with another of the herein described embodiments.

The products may be divided into any practical number of stages based upon the number of specific needs to be addressed by the product generally and the stages specifically. For example, an array may be provided with one or more products which correspond to 2 stages, to 3 stages, or to 4 stages. FIG. 1 illustrates an array of wipes products incorporating one wipes product tailored to correspond to one of three stages. FIG. 2 shows an alternative set of icons which may be used to communicate the stages to which each of a variety of products are tailored. A package icon for each stage, 60, 70 and 80, respectively, may include at least two forms of stage-specific indicia such as a label 66 and a graphic 67. Similarly, the package icons for later stages (such as a second stage) may include a second stage label 76 and a graphic 77. A third stage icon may include a third stage label 86 and a graphic 87. The series of graphics or icons may illustrate the evolving parent/child relationship as the child grows from newborn where the child is nursing and/or primarily eating formula, through a stage of initial mobility where the child is first eating solid foods such as cereal and/or jar foods, and to a stage of standing/first steps where the child is beginning to self-feed and to begin to eat table foods. The stage-related indicia may further contain characteristics to appeal to either the actual purchaser or a person associated with the purchaser. For example, the stage-specific indicia may focus on the parent in early stages and focus on the child in the later stages, as the child becomes more independent. Other labels and graphics may be chosen as well. Additionally, the indicia used to indicate stage may be arbitrary such a color or number scheme, although icons which tend to suggest attributes of the stage may be desirable.

Furthermore, the stage-specific indicia provided on the packaging may be based upon one or more the developmental characteristics of the child. That is, the stage-specific indicia may show at the first stage a child nursing while later stages may show the child progressing to spoon foods and then to solid foods. Similarly, the stage-specific indicia may relate to child activity. That is, the child may be shown swaddling at a first stage, exploring crawling at a second stage, standing or walking at a third stage and toilet training at a fourth stage.

The products may be arranged at a retailer environment within a single group of products separated into stages. A group of products disposed upon a shelf within a retail environment may be further divided into stages such as 4 stages. It is possible to have fewer stages such as two stages or three stages. There may be more than four stages if desired.

Identifying the number of stages and preparing packaging for stages assists a potential consumer in making a purchasing decision. The product associated with each stage may be tailored to correspond to particular performance needs associated with a given stage. Continuing with the cleansing wipes example, the product associated with each of a number of stages may have certain structural and component characteristics. For example, all are cleansing wipes, and therefore, the product for each stage will have a substrate useable as a cleansing wipe and some form of a cleaning lotion impregnated into the substrate. Each of these two basic components, however, may vary to correspond to the particular performance needs associated with a given stage development.

Diapers sold in stages have focused on the changing mobility and fit needs of babies and children in various stages. Examples of such approaches are described in U.S. Pat. Nos. 6,648,864 and 6,763,944. These disclosures provide additional detail regarding stage characteristics and methods of both tailoring products to stages and communicating such tailoring. Additionally, Co-pending patent application Ser. No. 11/066,091 filed on Feb. 25, 2005 describes wipes products having targeting sensory elements which vary by use situation and/or by stage of development. The arrays described herein may additionally focus on the changing diet and activities of the babies and children and the corresponding cleaning challenges associated with various stages of development. The arrays described herein may additionally focus on the structural differences among the wipes themselves that specifically address the different cleaning needs of the child in the difference stages of development.

Thus, it will be appreciated that a product may be designed and specified in view of development stages of a child. Moreover, the product packaging likewise may incorporate stage-specific indicia to direct a potential to the correct product for the particular developmental stage of the child. It will be appreciated that products other than those used in child care may incorporate stage-specific features in the product characteristics and product packaging.

While the foregoing detailed description relates to a particular product group cleansing wipes and multiple stages of product within that group, the concepts may be applied to virtually any product. Thus, the invention is not limited to the particular product group, multi-stage configuration, packaging indicia, and the like. The invention is only limited as defined by the following claims.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. An array of disposable cleaning wipes products for capturing the products of human bowel movements comprising:
   a first cleaning wipe product, a second cleaning wipe product, and a third cleaning wipe product;
   each of said first, second, and third cleaning wipe product containing a respectively first, second, and third substrate and aqueous compositions that are different from each other;
   said first, second, and third substrate having a respective first, second, and third texturing; said second texturing being more textured than said third texturing, and said third texturing being more textured than said first texturing;
   wherein each of said first, second, and third wipes is packaged separately in a respectively first, second, and third packaging; and
   wherein each of said first, second, and third packaging is provided with a respective first, second, and third indicia indicative of a respective and different first, second, and third diet consumed at a respective first, second, and third stage of human development.

2. The array of claim 1, wherein each of said first, second, and third cleaning wipe products has a respective first, second, and third scent level; said second scent level being greater than said third scent level, and said third scent level being greater than said first scent level.

3. The array of claim 1, wherein each of said first, second, and third cleaning wipe products has a respective first, second, and third lotion load; said second lotion load being greater than said first and third lotion loads.

4. The array of claim 1, wherein said first cleaning wipe product comprises a skin conditioning agent.

5. The array of claim 1, wherein said second cleaning wipe product comprises an anti-stick agent.

6. The array of claim 1, wherein said third cleaning wipe product comprises an anti-microbial agent.

7. The array of claim 1, wherein each of said first, second, and third packaging comprises a plurality of said first, second, and third cleaning wipe products, respectively.

8. The array of claim 1, further comprising a fourth cleaning wipe product containing a fourth substrate and aqueous composition different from said first, second, and third substrates and aqueous compositions; wherein the fourth cleaning wipe product is packaged separately in a fourth packaging, and wherein the fourth packaging is provided with an indicia indicative of a fourth diet consumed at a fourth stage of human development.

9. The array of claim 8, wherein the fourth substrate is flushable.

10. An array of disposable cleaning wipes products for capturing the products of human bowel movements comprising:
    a first cleaning wipe product, a second cleaning wipe product, and a third cleaning wipe product;
    each of said first, second, and third cleaning wipe product containing a respectively first, second, and third substrate and aqueous compositions that are different from each other;
    said first, second, and third substrate having a respective first, second, and third surfactancy; said second surfactancy being higher than said first and third surfactancies;
    wherein each of said first, second, and third wipes is packaged separately in a respectively first, second, and third packaging; and
    wherein each of said first, second, and third packaging is provided with a respective first, second, and third indicia indicative of a respective and different first, second, and third diet consumed at a respective first, second, and third stage of human development.

11. The array of claim 10, wherein each of said first, second, and third cleaning wipe products has a respective first, second, and third scent level; said second scent level being greater than said third scent level, and said third scent level being greater than said first scent level.

12. The array of claim 10, wherein each of said first, second, and third cleaning wipe products has a respective first, second, and third lotion load; said second lotion load being greater than said first and third lotion loads.

13. The array of claim 10, wherein said first cleaning wipe product comprises a skin conditioning agent.

14. The array of claim 10, wherein said second cleaning wipe product comprises an anti-stick agent.

15. The array of claim 10, wherein said third cleaning wipe product comprises an anti-microbial agent.

16. The array of claim 10, wherein each of said first, second, and third packaging comprises a plurality of said first, second, and third cleaning wipe products, respectively.

17. The array of claim 10, further comprising a fourth cleaning wipe product containing a fourth substrate and aqueous composition different from said first, second, and third substrates and aqueous compositions; the fourth substrate being flushable; wherein the fourth cleaning wipe product is packaged separately in a fourth packaging, and wherein the fourth packaging is provided with an indicia indicative of a fourth diet consumed at a fourth stage of human development.

18. The array of claim 17, wherein the fourth substrate is flushable.

19. The array of claim 10, wherein said first, second, and third substrate have a respective first, second, and third texturing; said second texturing being more textured than said third texturing, and said third texturing being more textured than said first texturing.

* * * * *